United States Patent [19]

Dimmel et al.

[11] Patent Number: 5,049,236

[45] Date of Patent: Sep. 17, 1991

[54] LIGNIN DERIVED QUINONIC COMPOUND MIXTURES USEFUL FOR THE DELIGNIFICATION OF CELLULOSIC MATERIALS

[75] Inventors: Donald R. Dimmel, Appleton; John C. Wozniak, Kimberly, Wis.

[73] Assignee: Institute of Paper Science and Technology, Inc., Appleton, Wis.

[21] Appl. No.: 235,316

[22] Filed: Aug. 23, 1988

[51] Int. Cl.$^5$ ................................................ D21C 3/20
[52] U.S. Cl. .......................................... 162/16; 162/72; 552/265; 552/270; 552/296; 552/298
[58] Field of Search ............................. 162/72, 14, 16; 552/265, 269, 270, 296, 298, 292

[56] References Cited

U.S. PATENT DOCUMENTS

| | | | |
|---|---|---|---|
| 1,303,168 | 5/1919 | Conover | 552/269 |
| 3,873,580 | 3/1975 | Rennie | 552/269 |
| 4,012,280 | 3/1977 | Holton | 162/72 |

OTHER PUBLICATIONS

Sarkanen et al, "*Lignins–Occurrence, Formation, Structure and Reactions*"; N.Y., Wiley & Sons, 1971, pp. 43–94.

Butz et al, "*Organic Reactions*", vol. V; N.Y., Wiley & Sons, 1949, p. 166.

*Primary Examiner*—Steve Alvo
*Attorney, Agent, or Firm*—Fitch, Even, Tabin & Flannery

[57] ABSTRACT

A method for the preparation of a mixture of fused ring quinone type compounds from lignin and lignin-derived substances. The mixture of fused ring quinone compounds has been found useful in the wood pulping process as an accelerator in the degradation and separation of wood lignin from the other principal wood constituents, cellulose and hemicellulose.

11 Claims, No Drawings

LIGNIN DERIVED QUINONIC COMPOUND MIXTURES USEFUL FOR THE DELIGNIFICATION OF CELLULOSIC MATERIALS

The invention relates to the preparation of a mixture of fused ring quinone type compounds from lignin and lignin derived substances. The mixture of fused ring quinone compounds has been found useful in the wood pulping process as an accelerator in the degradation and separation of wood lignin from the other principal wood constituents, cellulose and hemicellulose.

BACKGROUND OF THE INVENTION

The wood used in paper making consists essentially of cellulose and hemicellulose fibers bound together by a polymeric material called lignin. A goal of the chemically-based wood pulping processes is to separate the cellulose and hemicellulose from the lignin by degrading the lignin into lower molecular weight species that are soluble in water. In a typical pulping process, wood is added to an aqueous solution of an alkali such as sodium carbonate, sodium bicarbonate or sodium hydroxide, and the resulting mixture is heated under pressure to a temperature in the range of 140°180° C. While the wood lignin may be broken down by reaction with the alkali alone, the process is slow and also results in excessive degradation of the cellulose and hemicellulose which are the desired products. In order to shorten the processing time or lower the processing temperature or both, accelerators such as sodium sulfite or sodium sulfide are usually added to the alkali solution to aid in processing.

The sulfur based accelerators reduce the processing time and produce a product superior to that produced by alkali alone, but these additives also introduce additional problems. For example, for the sulfide (kraft) process, the resulting pulp material is dark and more difficult to bleach, malodorous air emissions may occur, and expensive chemical recovery equipment is needed in order to reduce chemical costs. While the sulfur containing systems do present several difficulties to the paper making industry, they are nonetheless the standard process used because they offer the overall greatest flexibility, low chemical costs and strongest paper. For example, the lignin containing black liquor from the pulping process is burned to produce heat, and the sulfur and caustic are recovered from the burner and recycled. Sulfur recovery, however, is a difficult process and represents a major problem to the industry.

An alternative to the use of sulfur accelerators was described by Holton in U.S. Pat. No. 4,012,280 in which he describes the addition and use of quinone compounds such as napthoquinone, anthraquinone, phenanthrenequinone, anthone and their ring substituted derivatives (collectively called AQ) as accelerators in the wood pulping process. The AQ compounds may be used to replace some, most or all of the sulfur compounds, thereby decreasing or eliminating the odor problems and costs of the sulfur compounds. However, while the AQ compounds solve two problems, they introduce the problem of their own: cost.

The preferred quinone in the Holton invention is anthraquinone. This chemical is retained in the black liquor when it is separated from the pulp product and cannot be economically removed from the liquor. When the black liquor is concentrated and burned for its fuel value, the anthraquinone is destroyed. The Holton invention thus has a non-returnable chemical cost associated with it. Even at the level of 0.1 wt. % of the wood pulp as described in the Holton patent, the cost of the AQ compounds is an economic deterrent to widespread use.

It is an object of this invention to provide a process whereby lignocellulosics, lignin and lignin derived compounds, such as may be found in in black liquor obtained by pulping wood, can be reacted to form a mixture of quinone compounds containing benzoquinones, napthoquinones, anthraquinones and phenanthrenequinones which can be added to the pulping process to accelerate the lignin degradation process.

DESCRIPTION OF THE INVENTION

From a simplistic viewpoint, lignin may be regarded as a polymeric aryl-alkyl ether of general formula $[-O-C_6H_{4-y}(OCH_3)_y CHCHCH_2OH]_x$, where $x$ is some large number greater than 1 and $y=0$, 1 or 2. During the delignification process, the lignin macropolymer is broken down into much shorter chain species and may be degraded so far as to form monomers and dimers. In actual fact, the so-called "black liquor" solution which results from the delignification process contains a complex mixture of lignin degradation products which can basically be described as phenolic and esterified phenolic groups of indeterminant molecular weight with generally one or two methoxy groups adjacent to the phenolic hydroxyl group and an alkyl side chain para to the phenolic hydroxyl group. Oxidation of the phenolic hydroxyl group and an adjacent methoxy group will produce an o-benzoquinone. Oxidation of the hydroxyl group and the alkyl group will produce a p-benzoquinone [See K. V. Sarkanen and C. H. Ludwig, eds., *Lignins-Occurrence, Formation, Structure and Reactions* (New York: J. Wiley & Sons, 1971), pp 43–94]. It is known that a small portion of the lignin in the wood pulp is converted into o- and p-benzoquinones during the pulping process. However, under the rather severe conditions employed during the process, these quinones are not effective as catalysts because they are attacked by the pulping reagents and degraded. In order to be effective as a pulping accelerator, the quinone must be relatively stable during the pulping process. In addition, there must be a balance between the quinone's affinity for water and for the wood pulp.

D. R. Dimmel, in J. Wood Chem. Technology, 5 (1985), 1–14, describes that pulping catalysts act through a redox cycle in which the catalyst is reduced by the cellulosic material and oxidized by the lignin. Thus, in order to facilitate the degradation of the lignin, the catalyst both must be capable of being adsorbed on the surface of the lignin and must have a redox potential which readily permits the interconversion between the oxidized and reduced forms.

Since the benzoquinone compounds are not sufficiently stable under pulping conditions to act as effective pulping acceleration catalysts, more stable quinone compounds having the proper balance of pulp affinity and redox potential must be used. Fused ring quinone compounds such as napthoquinone, anthraquinone, phenanthrenequinone and their derivatives offer the appropriate balance of properties. These fused ring compounds can be made from the benzoquinones and substituted benzoquinones by means of the Diels-Alder reaction with conjugated dienes. For example, one method of making anthraquinone involves reacting p-benzoquinone with two equivalents of 1,3-butadiene. The process involves three steps: the addition of the conjugated diene to the starting quinone, aromatization of the adduct, and oxidation of the resulting quinol to a quinone [L. W. Butz and A. W. Rytina, Organic Reactions, Vol. V (New York, John Wiley & Sons, 1949) 166].

Little is known, however, concerning the reaction of methoxy and 2,6-dimethoxy-p-benzoquinone. (The latter can be generated from lignin). It has been shown that methoxy-p-benzoquinone will react with 1,3-butadiene to give 2-methoxy-4a,5,8,8a-tetrahydronapthoquinone [G. I. Birnbaum, J. Org. Chem., 25, 1660-1, (1960)] and with 2,3-dimethyl-1,3-butadiene to give 5,8-dihydro-2-methoxy-6,7-dimethyl-1,4-napthoquinone [M. F. Ansell, J. Chem. Soc., 3020, (1963)]. A more recent publication has shown that 2,6-dimethoxy-p-benzoquinone can be combined with isoprene to give a mixture of 2-methoxy-6-methyl-1,4-napthoquinone and 2-methoxy-7-methyl-1,4-napthoquinone [I.-M. Teg-moLarsson, Tetra. Letters, 22, 2043-6, (1981)].

The final products obtained from reacting a diene with a quinone depend on the severity of the Diels-Alder reaction conditions (mainly temperature) and the nature of the oxidizing conditions. Higher temperatures and strong oxidants, such as chromic acid result in fully aromatized anthraquinone products such as 2,6-and 2,7-dimethylanthraquinone.

The benzoquinones mentioned above (methoxy- and 2,6-dimethoxy-p-benzoquinone and o-benzoquinones with a side chain) can be generated from lignin and lignin derived compounds through the use of several oxidative technique. We have found, for example, that 2,6-dimethoxy-p-benzoquinone can be generated and isolated directly through lignin oxidation with potassium nitrodisulfonate or peracetic acid. High yields of the benzoquinones can also be obtained from reaction of the lignin derived compounds vanillin and syringaldehyde, [this work, along with H. H. Nimz, Cellulose Chem. Technol., 13, 36–46 (1979); Japanese Patent No. 78 82,730 of July 21, 1978]. Examples of the reaction of dienes and benzoquinones are shown in Table 1 and examples using lignin model or derived compounds are shown in Table 2.

The Diels-Alder products obtained from benzoquinones, lignin and lignin derived compounds are effective pulping accelerators or catalysts. As compared to pulping without these additives, we have found a significant reduction in lignin content (Kappa Number) and enhanced cellulose and hemicellulose (carbohydrate) yield when pulping with catalytic amounts (such as 0.1 wt. % addition, based on dry wood) of the Diels-Alder reaction products. Lower Kappa Numbers are desirable. A few examples of the results obtained when pulping Southern pine are shown in Table 3.

TABLE 1

Diels-Alder Reactions of Methoxy- and 2,6-Dimethoxy-p-benzoquinone

| Quinone | Diene | Products |
|---|---|---|
| Methoxy-p-benzoquinone | 2,3-Dimethyl-1,3-butadiene | 2-Methoxy-6,7-dimethyl-1,4-naphthoquinone |
| Methoxy-p-benzoquinone | 2,3-Dimethyl-1,3-butadiene | 2,3,6,7-Tetramethylanthraquinone |
| Methoxy-p-benzoquinone | Isoprene | 6- and 7-Methyl-2-methoxy-1,4-naphthoquinone |
| Methoxy-p-benzoquinone | Isoprene | 2,6- and 2,7-Dimethylanthraquinone |
| 2,6-Dimethoxy-p-benzoquinone | 2,3-Dimethyl-1,3-butadiene | 2-Methoxy-6,7-dimethyl-1,4-naphthoquinone |
| 2,6-Dimethoxy-p-benzoquinone | 2,3-Dimethyl-1,3-butadiene | 2,3,6,7-Tetramethylanthraquinone |
| 2,6-Dimethoxy-p-benzoquinone | Isoprene | 6- and 7-Methyl-2-methoxy-1,4-naphthoquinone |
| 2,6-Dimethoxy-p-benzoquinone | Isoprene | 2,6- and 2,7-Dimethylanthraquinone |

TABLE 2

Diels-Alder Reactions of Quinones Generated from Lignin Model Compounds

| Compound[a] | Diene | Products |
|---|---|---|
| 4-Methylcatechol | Isoprene | 4,6- and 4,7-Dimethyl-5,8-dihydronaphthalene-1,2-diol |
| 4-Methylcatechol | Styrene | 4-Methyl-4a,5a,10,10a-tetrahydrophenanthrene-1,2-quinone |
| Acetovanillone | 2,3-Dimethyl-1,3-butadiene | 5,8-Dihydro-2,3,6,7-tetramethylphenanthrene-9,10-diol and 2,3,6,7-Tetramethylphenanthrene-9,10-quinone |
| Acetovanillone | Isoprene | 2,6-, 2,7-, 3,6-, and 3,7-Dimethyl-5,8-dihydrophenanthrene-9,10-diol and 2,6-, 2,7-, and 3,6-Dimethylphenanthrene-9,10-quinone |
| Alpha-Methylvanillyl Alcohol | 2,3-Dimethyl-1,3-butadiene | 2-Methoxy-6,7-dimethyl-1,4-naphthoquinone and 2,3,6,7-Tetramethyl-phenanthrene-9,10-quinone |
| Alpha-Methylvanillyl | Isoprene | 6- and 7-Methyl-2-methoxy-1,4-naphthoquinone |

[a] the compound is oxidized to a quinone prior to reaction with the diene.

TABLE 3

Pulping with Lignin-Derived Compounds[a]

| Compound | Addition Level (% on wood) | Kappa No. | Carbohydrate Yield (%) |
|---|---|---|---|
| 2-Methoxy-6,7-dimethyl-1,4-napthoquinone | 0.2 | 70.3 | 42.8 |
| 6- and 7-Methyl-2-methoxy-1,4-naphthoquinone | 0.1 | 68.6 | 43.2 |
| 2,6- and 2,7-Dimethyl-anthraquinone | 0.1 | 31.2 | 44.6 |
| 2,6- and 2,7-Dimethyl-anthraquinone | 0.05 | 35.2 | 44.0 |
| 5,8-Dihydro-2,3,6,7-tetramethylphenanthrene-9,10-diol | 0.1 | 66.5 | 42.0 |
| 2,6-, 2,7-, 3,6 and 3,7-dimethyl-5,8-dihydrophenanthrene-9,10-diol | 0.1 | 73.5 | 42.3 |
| No additive | — | 81.1 | 42.8 |

[a] Typical pulping conditions may be found in the following examples.

The use of quinones in the pulping process was described by Holton in U.S. Pat. No. 4,012,280 as described above. While Holton describes adding quinone to the pulping process, he does not describe, nor suggest, that the quinones could be generated from the lignin or lignin derived products, such as those that are present in the black liquor which is obtained during pulping. Holton simply purchases quinones from an outside source and continuously add them to the pulping mixture. In accord with this invention, lignin-containing substances, simple compounds related to lignin, and/or lignin derived substances from the pulping process are modified by oxidative and Diels-Alder reactions to generate a mixture of quinone compounds which are useful in accelerating or catalyzing delignification during the pulping process. The lignin derived substances may be oxidized directly in the pulping liquor, may be isolated and oxidized, or may be converted into other products (such as vanillin or syringaldehyde) which are oxidized and then Diels-Alder modified. Oxidation can be carried out using potassium nitrodisulfonate, peroxyacids such as peracetic acid or perbenzoic acid, hydrogen peroxide, chromic acid, perhalogenic acids and perhalogenate salts, potassium thiophenoxide, electrochemical methods and the like. The oxidation and Diels-Alder reactions can be carried out as separate steps or they can be combined in a single step. Finally, the quinols formed from the Diels-Alder reaction can be oxidized to the quinone form prior addition to the pulping mixture, or it can be added to the pulping mixture as the quinol, wherein it will be oxidized to the quinone form.

The method of the invention comprises the steps of mixing the lignin and lignin derived substances in a solvent which may be from the group consisting of water, $C_1$-$C_4$ organic acids, glycols and glycol ethers to form a lignin and lignin derived substances solution. It is not necessary that all the lignin substances be dissolved in the solution. The solution may contain suspended or particulate substances. The solution is then oxidized by the addition of an oxidizing agent selected from potassium nitrodisulfonate, peroxycarboxylic acids, hydrogen peroxide, chromic acid, perhalogenic acids, perhalogenate salts and thiophenoxide.

After oxidation, the reaction mixture is precipitated on ice and the lignin, lignin derived compounds, and quinones are collected by filtration. These products are then charged to a pressure vessel along with a $C_1$-$C_4$ carboxylic acid such as glacial acetic acid, and a conjugated diene, and heated to a temperature in the range of 75°-160° C. for a time in the range of 12-24 hours. The diene may be any conjugated diene. Some of the more useful of such compounds are 1,3-butadiene, 2,3-dimethyl-1,3-butadiene, isoprene, 1,3-cyclohexadiene, cyclopentadiene, and styrene. After reaction with the diene, the pressure vessel is vented and the reaction mass precipitated on ice and filtered to collect the products. The reaction products are then oxidized a second time with one of the oxidizing agents listed above, chromic acid being preferred, in order to convert the quinol formed during the diene reaction to the quinone form. The resulting mixture of quinones which can include benzoquinones, napthoquinones, anthraquinones and phenanthrenequinones is added to an alkali containing wood pulp mixture to facilitate, catalyze and accelerate the delignification of the wood contained therein.

In a preferred embodiment of this invention, the initial oxidation and Diels-Alder reactions are combined in one step. That is, the lignin and lignin derived substances, along with the diene, and a solvent are charged together to a reactor. The oxidizing agent is added and the reaction mixture is maintained at a temperature ranging from ambient to 160° C., depending on the reactivity of diene being used, for a time in the range of 12-24 hours. The remaining reactions may then be carried out as described above. In this example and that described above, the oxidation and Diels-Alder reactions are carried out in an inert atmosphere using a gas such as nitrogen.

In yet another embodiment of the invention, the reactions are stopped after the Diels-Alder reaction is complete and the quinol containing reaction mass is added to a wood pulp mixture wherein the quinol form is oxidized to the quinone form by the reactions therein.

The examples which follow are meant to illustrate the method for the delignification of wood utilizing fused ring quinone compounds prepared from lignin and lignin derived substances in the black liquor that results from the wood pulping process.

Also, the following examples are given to illustrate the general scope of the invention and are not intended to be limiting upon the invention.

EXAMPLE 1

Methoxy-p-benzoquinone (0.50 g) and 2,3-dimethyl-1,3-butadiene (0.63 ml) were added to 23.0 mL of glacial acetic acid. The mixture was heated at 45° C. for 18.5 hrs. A chromic acid solution consisting of 1.85 g of $Na_2Cr_2O_7.2H_2O$, 1.16 mL water, and 0.09 mL of concentrated $H_2SO_4$ was then added, and the temperature was kept at approximately 67° C. for 1 hour. The product was precipitated by the addition of ice water, washed several times with cold water, and then dried over $P_2O_5$. A 71% yield (0.557 g) of 2-methoxy-6,7-dimethyl-1,4-naphthoquinone was obtained.

Pulping with this additive was carried out in a 500-mL stainless steel pressure vessel using Southern pine chips with a moisture content of 11.8%. The following conditions were used:

| | |
|---|---|
| Oven dry wood (g) | 35.0 |
| Additive (% on wood) | 0.2 |
| NaOH, as $Na_2O$ (% on wood) | 4.0 |
| Cooking schedule: | |
| Time at 90° C. (min.) | 15 |
| Time from 90° C. to 173° C. (min.) | 90 |
| Time at 173° C. (min.) | 95 |
| H-factor | 2100 |

Following pulping, a Kappa Number of 70.3 and a carbohydrate yield of 42.8 were obtained.

EXAMPLE 2

An isomeric mixture of 2,6- and 2,7-dimethylanthraquinone was obtained by combining 0.20 g of 2,6-dimethoxy-p-benzoquinone and 0.30 mL of isoprene with 3.0 mL of glacial acetic acid in a 4.5-mL stainless steel bomb. The bomb was heated at 60° C. for 30 minutes and then at 180° C. for 24 hr with slow rotation. This was followed by oxidation with chromic acid and precipitation of the product with ice water as described above; the yield was approximately 25%.

Pulping with the dimethylanthraquinone mixture was carried out as described in Example 1 but using 0.05% additive. A Kappa Number of 35.2 and a carbohydrate yield of 44.0 were obtained.

EXAMPLE 3

2-Methoxy-6,7-dimethyl-1,4-naphthoquinone was obtained from alpha-methylvanillyl alcohol (a lignin model compound) by combining the oxidation and Diels-Alder reactions into one step. Sodium periodate (0.64 g) in 7 mL of distilled water was added to 0.50 g of alpha-methylvanillyl alcohol dissolved in 7 mL of glacial acetic acid, followed immediately by the addition of 7 mL of 2,3-dimethyl-1,3-butadiene. After 1 minute, 1 mL of ethylene glycol was added to consume any unreacted sodium periodate. The reaction was then allowed to proceed in the dark as 25° C. for 3 hr. The reaction mixture was then extracted with $CHCl_3$, and the extract was washed with a saturated $NaHCO_3$ solution and with water, and dried over anhydrous $Na_2SO_4$. The solid remaining after evaporation of the solvent under reduced pressure was immediately dissolved in hot methanol. Upon cooling, 2-methoxy-6,7-dimethyl-1,4-naphthoquinone crystallized; it was washed with cold methanol and dried. Recrystallized yield was 0.093 g (14%).

When this reaction was repeated at 45° C. for 18.5 hr and followed by chromic acid oxidation as described in Example 1, product analysis indicated the formation of 2,3,6,7-tetramethylphenanthrene-9,10-quinone as well as 2-methoxy-6,7-dimethyl-1,4-naphthoquinone.

EXAMPLE 4

2,6-Dimethoxy-p-benzoquinone was obtained directly from lignin through oxidation with potassium nitrosodisulfonate. A 200-mg hardwood lignin sample was dissolved in 10 mL of ethylene glycol monomethyl ether in a 50-mL Erlenmeyer flask which was then cooled to approximately 0° C. in an ice bath. Under a stream of nitrogen, 3.0 mmole of potassium nitrosodisulfonate was added to 20.0 mL of a 0.2M $KH_2PO_4$ - $K_2HPO_4$ buffer solution (pH=6.0) which had also been cooled in an ice bath. This mixture was then added dropwise to the lignin solution with fairly vigorous stirring, again using a stream of nitrogen to blanket the reaction.

The reaction mixture was removed from the ice bath and allowed to come to room temperature. Total reaction time was approximately 2 hours. The product was obtained by extraction with chloroform; the yield of 2,6-dimethoxy-p-benzoquinone, determined by gas chromatographic techniques, was approximately 4%. Reaction with isoprene as in Example 2 leads to the formation of 2,6- and 2,7-dimethylanthraquinone. Pulping with the resulting dimethylanthraquinone will give a Kappa Number and carbohydrate yield similar to those obtained in Example 2.

EXAMPLE 5

Combining the oxidation and Diels-Alder reactions of lignin led to the production of a mixture of several quinone compounds. A 400-mg hardwood lignin sample was oxidized as described in Example 4, except that 1.0 ml of isoprene was added just prior to the addition of the potassium nitrosodisulfonate. Following the oxidation, the reaction mixture was transferred to a 140-ml stainless steel pressure vessel, 25 ml of glacial acetic acid was added, and temperature was raised to 112° C. for 18 hours.

The resulting mixture was poured onto ice to precipitate the lignin; the lignin was collected and washed in cold water, using centrifugation and filtering through a fine sintered-glass funnel to prevent the loss of small particles. The lignin was then transferred to a 25-ml, round-bottom flask with 10 ml of glacial acetic acid, and chromic acid oxidation was conducted by adding 0.46 g of $Na_2Cr_2O_7 \cdot 2H_2O$, 0.29 ml of $H_2O$, and 0.02 ml of concentrated $H_2SO_4$ and then raising the temperature to 67° C. for 30 min. Finally, the lignin was again isolated as just described.

Analysis of the chloroform extracts of the liquids remaining after precipitation of the lignin indicated the generation of 2,6-dimethoxy-p-benzoquinone and Diels-Alder adducts resulting from the addition of both one and two units of isoprene.

What is claimed is:

1. A method for the preparation of a fused ring substance, the fused ring substance is useful for the delignification of cellulosic materials and being prepared by the method comprising the steps of:
   a) oxidizing a the lignin substance or a lignin derived substance in a solvent by means of a first oxidizing agent to form a mixture of a first quinone product, wherein the first quinone product contains methoxy-substituted benzoquinone;
   b) reacting the first quinone product containing the methoxy-substituted benzoquinone with a diene according to the Diels-Alder reaction to form a mixture of fused ring quinone and fused ring quinol products; and
   c) oxidizing the mixture of fused ring quinone product and fused ring quinol products to form a final mixture of fused ring quinone compounds by means of a second oxidizing agent.

2. A method in accordance with claim 1 wherein the solvent is selected from the group consisting of water, $C_1$-$C_4$ organic acids, glycols and glycol ethers.

3. A method in accordance with claim 1 in which the first oxidizing agent is selected from the group consisting of potassium nitrodisulfonate, hydrogen peroxide, peroxycarboxylic acids, perhalogen acids, perhalogenate salts, chromic acid and potassium thiophenoxide.

4. A method in accordance with claim 1 wherein the second oxidizing agent is chromic acid.

5. A method in accordance with claim 1 wherein the diene is a conjugated diene selected from the group consisting of 1,3-butadiene, styrene, 2,3-dimethyl-1,3-butadiene, 1,3-cyclohexadiene, cyclopentadiene and isoprene.

6. A method in accordance with claim 1 wherein the mixture of fused ring quinone compounds consists of a mixture of substituted and unsubstituted napthoquinones, anthraquinones, and phenanthrenequinones.

7. The method in claim 1 wherein the fused ring quinol made in step b) is added to a pulping mixture and is then oxidized in the pulping mixture to the fused ring quinone compounds.

8. A method for the preparation of fused ring quinone compounds from lignin and lignin derived substances, the fused ring quinone compounds being useful for the delignification of cellulosic materials, and being prepared by the method comprising the steps of:
   a) dissolving the lignin and lignin derived substances in a solvent selected from the group consisting of water, $C_1$ to $C_4$ organic acids, glycols and glycol ethers to form a lignin and lignin derived compound solution;
   b) oxidizing the lignin and lignin derived substances in an inert atmosphere to monocyclic quinone compounds by means of a first oxidizing agent selected from the group consisting of potassium nitrodisulfonate, hydrogen peroxide, chromic acid, perhalogenic acids, perhalogenate salts, peroxycarboxylic acids and thiophenoxide;

c) warming the monocyclic quinone containing solution to ambient temperature and charging said solution to a pressure vessel;
d) adding a diene selected from the group consisting of 1,3-butadiene, 2,3-dimethyl-1,3-butadiene, isoprene, 1,3-cyclohexadiene, cyclopentadiene and styrene to the monocyclic quinone containing solution;
e) pressurizing the monocyclic quinonediene reaction mixture in a vessel under an inert atmosphere in the presence of an organic acid for a time in the range of about 12-24 hours to form fused ring quinol compounds;
f) cooling the reaction mixture to ambient temperature and isolating the lignin and lignin derived diene reaction products by precipitating the reaction mass on ice and collecting the product;
g) reacting the collected product in a C1-C4 carboxylic acid solution with a second oxidizing agent selected from the group consisting of potassium nitrodisulfonate, hydrogen peroxide, peroxycarboxylic acids, chromic acid, perhalogenic acids, perhalogenate salts and thiophenoxide to form a mixture of fused ring quinone compounds; and
h) isolating the resulting mixture of fused ring quinone compounds by precipitation on ice and collecting the product.

9. A method in accordance with claim 8 wherein the second oxidizing agent is chromic acid.

10. A method in accordance with claim 8 wherein the product fused ring quinone compounds are a mixture of substituted and unsubstituted naphthoquinones, anthraquinones and phenanthrenequinones.

11. A method in accordance with claim 8 wherein the carboxylic acid and peroxycarboxylic acid are glacial acetic acid, and peracetic acid and perbenzoic acid respectively.

* * * * *

UNITED STATES PATENT AND TRADEMARK OFFICE
CERTIFICATE OF CORRECTION

PATENT NO. : 5,049,236

DATED : September 17, 1991

INVENTOR(S) : Dimmel et al.

It is certified that error appears in the above-identified patent and that said Letters Patent is hereby corrected as shown below:

Column 1, line 55, change "napthoquinone" to --naphthoquinone--.
Column 1, line 56, change "anthone" to --anthrone--.
Column 2, line 12, change "napthoquinones" to --naphthoquinones--.
Column 2, line 28, change "indeterminant" to --indeterminate--.
Column 2, line 63, change "napthoquinone" to --naphthoquinone--.
Column 3, lines 13-14, change "tetrahydronapthoquinone" to --tetrahydronaphthoquinone--.
Column 3, lines 16-17, change "1,4-napthoquinone" to --naphthoquinone--.
Column 3, line 20, change "1,4-napthoquinone" to --naphthoquinone--.
Column 3, line 21, change "1,4-napthoquinone" to --naphthoquinone--.
Column 4, line 51, change "1,4-napthoquinone" to --naphthoquinone--.
Column 5, line 58, change "napthoquinone" to --naphthoquinone--.

UNITED STATES PATENT AND TRADEMARK OFFICE
CERTIFICATE OF CORRECTION

PATENT NO. : 5,049,236
DATED : September 17, 1991
INVENTOR(S) : Dimmel et al.

It is certified that error appears in the above-identified patent and that said Letters Patent is hereby corrected as shown below:

Claim 3, Column 8, line 34, change "perhalogen" to --perhalogenic--.
    Claim 6, Column 8, lines 46-47, change "napthoquinone" to --naphthoquinone--.
    Claim 8, Column 9, line 9, change "quinonediene" to --quinone-diene--.

Signed and Sealed this

Fourth Day of May, 1993

Attest:

MICHAEL K. KIRK

*Attesting Officer*    *Acting Commissioner of Patents and Trademarks*